United States Patent
Lin et al.

(10) Patent No.: US 10,945,888 B2
(45) Date of Patent: Mar. 16, 2021

(54) INTELLIGENT BLIND GUIDE METHOD AND APPARATUS

(71) Applicant: CLOUDMINDS (SHENZHEN) ROBOTICS SYSTEMS CO., LTD., Shenzhen (CN)

(72) Inventors: Yimin Lin, Beijing (CN); Shiguo Lian, Beijing (CN)

(73) Assignee: CLOUDMINDS (SHENZHEN) ROBOTICS SYSTEMS CO., LTD., Shenzhen (CN)

( * ) Notice: Subject to any disclaimer, the term of this patent is extended or adjusted under 35 U.S.C. 154(b) by 0 days.

(21) Appl. No.: 16/435,255

(22) Filed: Jun. 7, 2019

(65) Prior Publication Data
US 2019/0290493 A1 Sep. 26, 2019

Related U.S. Application Data

(63) Continuation of application No. PCT/CN2016/108928, filed on Dec. 7, 2016.

(51) Int. Cl.
*A61F 9/08* (2006.01)
*G01S 15/89* (2006.01)
(Continued)

(52) U.S. Cl.
CPC ............ *A61F 9/08* (2013.01); *A61H 3/06* (2013.01); *G01S 15/89* (2013.01); *G06F 3/011* (2013.01)

(58) Field of Classification Search
CPC ... G10L 15/22; G10L 2015/223; G10L 15/08; G10L 15/24; G10L 15/26; G10L 17/00;
(Continued)

(56) References Cited

U.S. PATENT DOCUMENTS

| 6,847,892 B2 * | 1/2005 | Zhou | G01S 5/0027 |
| | | | 340/426.1 |
| 9,348,336 B2 * | 5/2016 | Sisbot | G05D 1/0214 |

(Continued)

FOREIGN PATENT DOCUMENTS

| CN | 101514903 A | 8/2009 |
| CN | 101518482 A | 9/2009 |

(Continued)

OTHER PUBLICATIONS

International Search Report, for International Application No. PCT/CN2016/108928, dated Jul. 28, 2017, 5 pages.
(Continued)

*Primary Examiner* — Dave Czekaj
*Assistant Examiner* — Kehinde Abimbola
(74) *Attorney, Agent, or Firm* — Seed IP Law Group LLP (57) ABSTRACT

The embodiment of the present disclosure discloses an intelligent blind guide method and apparatus, and relates to the field of artificial intelligence, so as to solve the problem that an intelligent blind guide system requires the whole-process intervention of an artificial customer service staff, which results in high work intensity. The intelligent blind guide method includes: obtaining a confidence of an intelligent blind guide according to sensor information, wherein the confidence indicates the reliability of blind guide information generated according to the sensor information without artificial decision; generating the blind guide information according to the sensor information if the confidence is greater than or equal to a preset threshold, and importing artificial decision to generate the blind guide information if the confidence is less than the preset threshold. The embodiment of the present disclosure is applied to a blind guide helmet.

18 Claims, 3 Drawing Sheets

(51) Int. Cl.
*G06F 3/01* (2006.01)
*A61H 3/06* (2006.01)

(58) Field of Classification Search
CPC ......... G10L 2015/088; G10L 2015/228; G10L 15/00; G10L 15/02; G10L 15/063; G10L 15/18; A61F 9/08; A61H 3/06; G01S 15/89; G06F 3/011
See application file for complete search history.

(56) References Cited

U.S. PATENT DOCUMENTS

| | | | |
|---|---|---|---|
| 9,817,395 B2* | 11/2017 | Sisbot | G05D 1/0027 |
| 2003/0149526 A1* | 8/2003 | Zhou | G01S 5/0027 |
| | | | 701/408 |
| 2011/0150324 A1* | 6/2011 | Ngan | G06K 9/00704 |
| | | | 382/159 |
| 2012/0327203 A1 | 12/2012 | Oh et al. | |
| 2013/0201308 A1* | 8/2013 | Tan | G09B 21/00 |
| | | | 348/62 |
| 2016/0077526 A1* | 3/2016 | Sisbot | G06Q 50/01 |
| | | | 701/23 |
| 2017/0285635 A1* | 10/2017 | Sisbot | G05D 1/0027 |

FOREIGN PATENT DOCUMENTS

| | | |
|---|---|---|
| CN | 102385698 A | 3/2012 |
| CN | 103312899 A | 9/2013 |
| CN | 203328997 U | 12/2013 |
| CN | 105078717 A | 11/2015 |
| CN | 105591882 A | 5/2016 |
| CN | 105686936 A | 6/2016 |
| CN | 106021403 A | 10/2016 |
| JP | 2015-169505 A | 9/2015 |
| WO | 9521595 A1 | 8/1995 |

OTHER PUBLICATIONS

Atsushi Imazu, "Walking Guidance System for Visually Impaired Using Cloud Technology," Annual Meeting of the Japanese Society for Artificial Intelligence (28th) Proceedings, 2014.

Takeshi Kurata et al., "Navigation System for Visually Impaired Pedestrains-Preliminary Evaluation of Positioning Measurement and Obstacle Detection," Shingaku Giho, 2010, vol. 110, No. 238, pp. 67-72.

* cited by examiner

INTELLIGENT BLIND GUIDE METHOD AND APPARATUS

CROSS-REFERENCE TO RELATED APPLICATIONS

This application is a continuation application under 35 U.S.C. § 120 of and claims priority to PCT application No. PCT/CN2016/108928 filed on Dec. 7, 2016, the contents of which are all incorporated herein by reference.

FIELD OF THE DISCLOSURE

The present disclosure relates to the field of artificial intelligence, and in particular to an intelligent blind guide method and apparatus.

BACKGROUND OF THE DISCLOSURE

Artificial intelligence technology has developed rapidly and may replace some of work done by humans, but it is still limited to special application occasions such as simple tasks and single scenarios. For intelligent products with high reliability requirements, manual attention is still needed, thus consuming a large amount of manpower and material resources. For example, for an intelligent blind guide system, since the surrounding environments during a blind guide process are very complicated, the existing intelligent blind guide system still requires whole-process intervention of an artificial customer service staff during its use by a user, so that the work intensity of the artificial customer service staff is very high.

BRIEF SUMMARY

The embodiment of the present disclosure provides an intelligent blind guide method and apparatus, for mainly solving the problem that an intelligent blind guide system requires the whole-process intervention of an artificial customer service staff, resulting in high work intensity.

In order to achieve the above object, the embodiment of the present disclosure adopts the following technical solutions:

In a first aspect, an intelligent blind guide method is provided, including: obtaining a confidence of an intelligent blind guide according to sensor information, wherein the confidence of the intelligent blind guide indicates the reliability of blind guide information generated by processing the sensor information by using an artificial intelligence algorithm; and processing the sensor information by using the artificial intelligence algorithm to generate the blind guide information in a case that the confidence of the intelligent blind guide is greater than or equal to a preset threshold, and triggering an artificial blind guide in a case that the confidence of the intelligent blind guide is less than the preset threshold.

In a second aspect, an intelligent blind guide apparatus is provided, including: a calculation unit, configured to obtain a confidence of an intelligent blind guide according to sensor information, wherein the confidence of the intelligent blind guide indicates the reliability of blind guide information generated by processing the sensor information by using an artificial intelligence algorithm; and a judgment unit, configured to process the sensor information by using the artificial intelligence algorithm to generate the blind guide information in a case that the confidence of the intelligent blind guide is greater than or equal to a preset threshold, and configured to trigger an artificial blind guide in a case that the confidence of the intelligent blind guide is less than the preset threshold.

In a third aspect, a computer storage medium is provided for storing a computer software instruction used by an intelligent blind guide apparatus and the computer software instruction includes a program code designed to execute the intelligent blind guide method in the first aspect.

In a fourth aspect, a computer program product is provided, which is capable of being directly loaded in an internal memory of a computer and contains a software code, and the computer program can implement the intelligent blind guide method in the first aspect after being loaded and executed by the computer.

In a fifth aspect, a server is provided, including a memory, a communication interface and a processor, wherein the memory is configured to store a computer executable code, the processor is configured to execute the computer executable code to control the execution of the intelligent blind guide method in the first aspect, and the communication interface is configured to perform data transmission between the server and an external device.

According to the intelligent blind guide method and apparatus disclosed in the embodiment of the present disclosure, the confidence of the intelligent blind guide is obtained according to the sensor information, and no artificial intervention is needed in a case that the confidence is relatively high, and a blind guide function with higher reliability may be achieved only through the intelligent blind guide, thereby solving the problem that the intelligent blind guide system requires the whole-process intervention of the artificial customer service staff, which results in high work intensity. Meanwhile, the task failure caused by errors of the intelligent system is reduced.

BRIEF DESCRIPTION OF THE DRAWINGS

To illustrate technical solutions in the embodiments of the present disclosure or the prior art more clearly, a brief introduction of the drawings which are needed in the description of the embodiments or the prior art is given below. It will be apparent to those of skill in the art that the drawings in the description below are merely some of the embodiments of the present disclosure, based on which other drawings may be obtained by those of ordinary skills in the art without any creative effort.

DETAILED DESCRIPTION OF THE DISCLOSURE

A clear and complete description of technical solutions in the embodiments of the present disclosure will be given below, in combination with the drawings in the embodiments of the present disclosure. It will be apparent to one of skill in the art that the embodiments described below are merely a part, but not all, of the embodiments of the present disclosure. All other embodiments, obtained by those of ordinary skills in the art based on the embodiments of the present disclosure without any creative effort, fall into the protection scope of the present disclosure.

Figure 1:
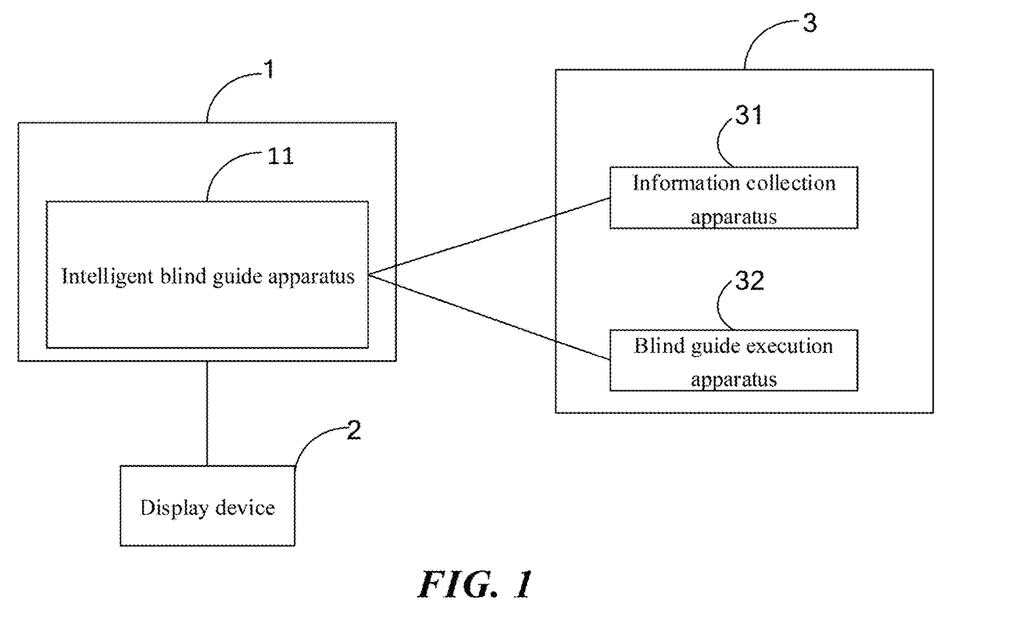
FIG. 1 is a structural schematic diagram of an intelligent blind guide system provided by an embodiment of the present disclosure.

The embodiment of the present disclosure provides an intelligent blind guide system, as shown in FIG. 1, including: a server 1 and a corresponding display device 2 located in the cloud, and a terminal 3 located on site. The server 1 includes an intelligent blind guide apparatus 11, and according to different actual application scenarios, the terminal 3 may be an intelligent device (for example, a mobile phone, a helmet or the like) that incorporates information collection and presentation functions and/or components, which may include an information collection apparatus 31 and a blind guide execution apparatus 32. The information collection apparatus 31 may be, for example, a visual sensor, an ultrasonic sensor or the like and is configured to collect sensor information; the blind guide execution apparatus 32 may be an apparatus for executing a blind guide action such as a sound player, a tactile feedback apparatus or the like. The information collection apparatus 31 collects the sensor information and sends the collected sensor information and/or data generated from the sensor information to the server 1 in a wired (for example, a cable, a network cable) or a wireless (for example, WIFI, Bluetooth) manner, and then the sensor information may be displayed on the display device 2, and then the intelligent blind guide apparatus 11 of the server 1 sends blind guide information to the blind guide execution apparatus 32 of the terminal 3 after performing decision making actions based on the sensor information. The blind guide execution apparatus 32 executes a blind guide action according to the blind guide information, for example, indicating to avoid an obstacle, to turn left, to stop advance, and the like.

According to the intelligent blind guide method and apparatus provided by the embodiment of the present disclosure, the reliability of the intelligent blind guide without artificial intervention is evaluated according to the obtained sensor information, and the intelligent blind guide without artificial intervention, e.g., human action from customer service, is adopted in a case that the reliability is higher, thereby solving the problem that the intelligent blind guide system requires the whole-process intervention of a human customer service staff, which human intervention results in high work intensity.

Figure 2:
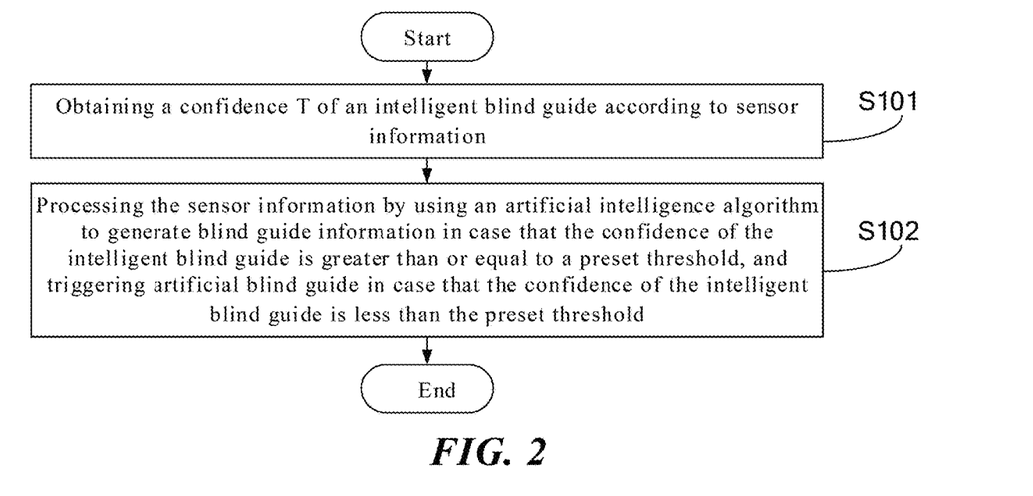
FIG. 2 is a schematic flow diagram of an intelligent blind guide method provided by an embodiment of the present disclosure.

The embodiment of the present disclosure provides an intelligent blind guide method, as shown in FIG. 2, including:

S101. Obtaining a confidence T of an intelligent blind guide according to sensor information, wherein the confidence of the intelligent blind guide indicates the reliability of blind guide information generated by processing the sensor information by using an artificial intelligence algorithm.

Specifically, the sensor information includes, but is not limited to, information about visual, auditory, distance, illumination and the like applied to the intelligent blind guide, and in a case that the sensor includes a visual sensor and an ultrasonic sensor, visual sensor information may be obtained through the visual sensor, and ultrasonic sensor information may be obtained through the ultrasonic sensor.

In an embodiment, the confidence is a probability value, and different evaluation methods, such as similarity, classification probability and the like, may be adopted according to different application scenarios.

The intelligent blind guide process may be executed by multiple specific modules according to functions. For example, a positioning module, an obstacle avoidance module and an identification module may be included, the positioning module obtaining a positioning accuracy confidence $T_L$ according to the sensor information, the obstacle avoidance module obtaining an obstacle avoidance success confidence $T_O$ according to the sensor information, the identification module obtaining an object identification confidence $T_R$ according to the sensor information, that is, at least two kinds of following confidences are obtained according to the sensor information: the positioning accuracy confidence, the obstacle avoidance success confidence and the object identification confidence, and then, the confidence T of the intelligent blind guide may be obtained by fusing the at least two kinds of confidences among the positioning accuracy confidence $T_L$, the obstacle avoidance success confidence $T_O$ and the object identification confidence $T_R$, for example, $T=T_O+T_R+T_L$. Those skilled in the art will also appreciate that other functions for executing the intelligent blind guide may have corresponding confidences for evaluating the reliability of the corresponding functions.

The positioning accuracy confidence may be obtained by means of texture quality, number of tracking, quality of motion and the like.

Specifically, the texture quality may be used for describing whether the features of a scene are rich, whether the light is insufficient, whether the scene is occluded, or the like. The specific method is to perform feature extraction on an image, such as feature point extraction or edge extraction, to describe the quality of the image texture. For the feature point extraction, if the number of the feature points is n, and it is assumed that the number of the feature points is at most N (n<=N), then the texture quality=n/N, and it can be seen that the value range is 0-1. The edge extraction is similar to the feature extraction described above. A binary image is obtained through the edge extraction, an area value of gradient response on the image is 1, and the remaining area is 0, then the number of pixels counted as 1 is n, and the number of wide multiplying high pixels of the image is N, then the texture quality=n/N, and it can be seen that the value range is also 0-1.

Specifically, the number of tracking may be used for describing the positioning quality of a vSLAM module. The specific method is based on the vSLAM of the feature point, each positioning result of the vSLAM is based on the calculation result of a certain number of feature points, so the more the feature points are, the more reliable the vSLAM is. Assuming that the number of tracked feature points is defined as n, and the number of tracked feature points is at most N (n<=N), then the tracking quality=n/N, and it can be seen that the value range is 0-1.

Specifically, the quality of motion is used for describing the speed of the camera motion, and if the speed is too high, image blur is caused easily. vSLAM may output the positioning results L1 and L2 of two frames in tandem, then according to the time interval s of the two frames, the speed of displacement is estimated as v=(L1−L2)/s. Assuming that the maximum speed is $v_m$, then the quality of motion=$v/v_m$, and it can be seen that the value range is 0-1 (in case that $v>v_m$, the value is 1).

Figure 3:
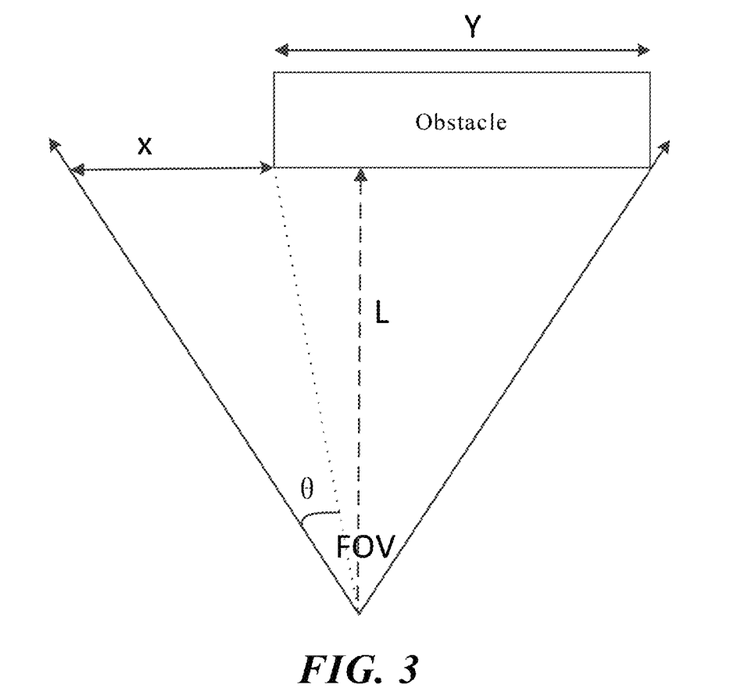
FIG. 3 is a schematic diagram of an obstacle avoidance success confidence provided by an embodiment of the present disclosure.

For the obstacle avoidance success confidence, an obstacle avoidance algorithm analyses a size ratio of a passable area in a scene view based on a depth reconstruction result. The specific steps are as follows: firstly, obtaining depth information by using a depth sensor, then dividing an area of an obstacle based on the depth information, then calculating the width of the passable area in the entire field of view (FOV) to serve as the confidence of obstacle avoidance, as shown in FIG. 3, X, Y and L are known according to the depth obstacle division result, assuming H=(X+Y)/2, the angle α of ½ FOV is α=arctan (H/L), θ=α−arctan[(H−X)/L], then the obstacle avoidance success confidence is defined as θ/2α, and it can be seen that the value range is 0~1.

The object identification confidence is used for describing an object identification result and belongs to a similarity index in pattern identification. The common implementation is as follows: a camera captures image information, after feature extraction, x is used for matching with a trained feature library y, and a measurement index for matching may be described by the distance between x and y, such as Euclidean distance, Manhattan distance, Chebyshev distance, Minkowski distance, standardized Euclidean distance, Mahalanobis distance, included angle cosine and Hamming distance or the like. The identification similarity may also be calculated by using a depth learning module, and a probability value of each node is comprehensively outputted to serve as the confidence.

S102. In a case that the confidence of the intelligent blind guide is greater than or equal to a preset threshold, the sensor information is processed by using the artificial intelligence algorithm to generate the blind guide information, and in a case that the confidence of the intelligent blind guide is less than the preset threshold, the artificial blind guide is triggered.

For example, in a case that the module for executing the intelligent blind guide includes the positioning module, the obstacle avoidance module and the identification module, if the confidence of the intelligent blind guide is greater than or equal to the preset threshold, it indicates that an intelligent blind guide mode without artificial intervention may be adopted, that is, a reliable blind guide indication may be given, in this case, generating the blind guide information according to the sensor information may specifically include any one or more of the following information: the positioning module generates current position coordinates according to the sensor information, the obstacle avoidance module generates a current travelable direction according to the sensor information, and the identification module generates an object identification tag according to the sensor information and the like. The above blind guide information may be fed back to a blind guide helmet in a wired or wireless manner to execute the blind guide.

If the confidence of the intelligent blind guide is less than the preset threshold, it means that it is difficult to give a reliable blind guide indication by relying solely on the intelligent blind guide mode without artificial intervention, in this case, artificial intervention is required for the blind guide, a human customer service staff is automatically called, and judgment and decision are performed depending on the background human customer service staff.

According to the intelligent blind guide method provided by the embodiment of the present disclosure, the confidence of the intelligent blind guide is obtained according to the sensor information. If the confidence is relatively high, no artificial intervention is needed, and a blind guide function with higher reliability may be achieved only through the intelligent blind guide, thereby solving the problem that the intelligent blind guide system requires the whole-process intervention of the human customer service staff, which results in high work intensity. Meanwhile, the task failure caused by errors of the intelligent system is reduced.

Those skilled in the art will readily appreciate that the present disclosure may be implemented by hardware or a combination of hardware and computer software in combination with the units and algorithm steps of the various examples described in the embodiments disclosed herein. Whether a certain function is implemented in the form of hardware or in the form of computer software driving hardware depends on the specific applications and design constraint conditions of the technical solutions. Those skilled in the art may implement the described functions by using different methods for each specific application, but this implementation should not be considered beyond the scope of the present disclosure.

The embodiment of the present disclosure may divide the function modules of the intelligent blind guide apparatus according to the above method example, for example, the function modules may be divided according to the functions, and two or more functions may also be integrated into one processing module. The above integrated module may be implemented in the form of hardware and may also be implemented in the form of a software function module. It should be noted that the division of the modules in the embodiment of the present disclosure is schematic and is only a logical function division, and other division manners may be provided during the actual implementation.

Figure 4:
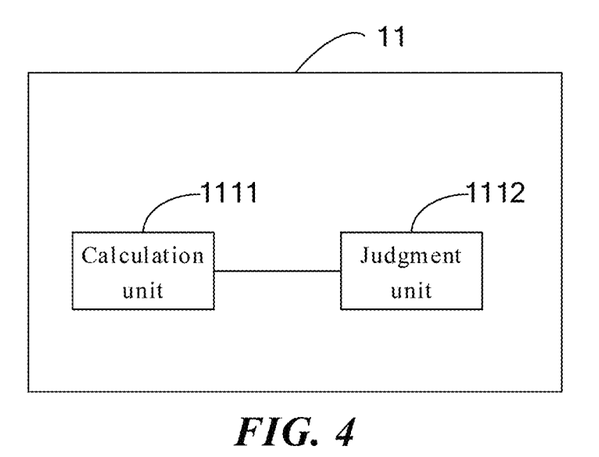
FIG. 4 is a structural schematic diagram of an intelligent blind guide apparatus provided by an embodiment of the present disclosure.

In the case that the function modules are divided according to the functions, FIG. 4 shows a possible structural schematic diagram of the intelligent blind guide apparatus involved in the above embodiment, the intelligent blind guide apparatus 11 includes a calculation unit 1111 and a judgment unit 1112. The calculation unit 1111 is configured to support the intelligent blind guide apparatus 11 to execute the process S101 in FIG. 2; and the judgment unit 1112 is configured to support the intelligent blind guide apparatus 11 to execute the process S102 in FIG. 2. All the related contents of the steps involved in the foregoing method embodiment may be quoted to the function descriptions of the corresponding function modules, and thus details are not described herein again.

Figure 5:
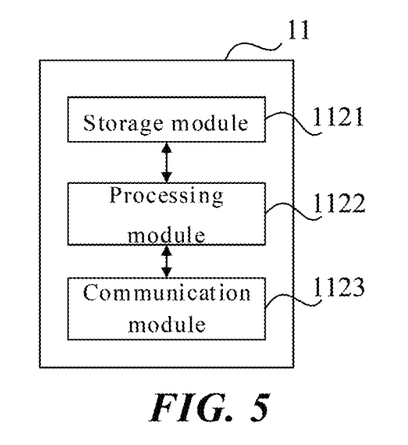
FIG. 5 is a structural schematic diagram of another intelligent blind guide apparatus provided by an embodiment of the present disclosure.

In the case that the integrated unit is adopted, FIG. 5 shows a possible structural schematic diagram of the intelligent blind guide apparatus involved in the above embodiment. The intelligent blind guide apparatus 11 includes a processing module 1122 and a communication module 1123. The processing module 1122 is configured to perform control and management on the actions of the intelligent blind guide apparatus, for example, the processing module 1122 is configured to support the intelligent blind guide apparatus to execute the processes S101-S102 in FIG. 2. The communication module 1123 is configured to support the communication between the intelligent blind guide apparatus and other entities, such as the communication between the intelligent blind guide apparatus and the functional modules or network entities as shown in FIG. 1. The intelligent blind guide apparatus 11 may further include a storage module 1121, configured to store a program code and data of the intelligent blind guide apparatus.

The processing module 1122 may be a processor or a controller, for example, a central processing unit (CPU), a general purpose processor, a digital signal processor (DSP), an application-specific integrated circuit (ASIC), a field programmable gate array (FPGA) or other programmable logic devices, transistor logic devices, hardware components, or any combinations thereof. The processing module may implement or execute logic boxes, modules and circuits of various examples described in combination with the contents disclosed by the present disclosure. The processor may also be a combination for implementing a computing function, for example, one or more microprocessor combinations, a combination of a DSP and a microprocessor, and the like. The communication module 1123 may be a transceiver, a transceiver circuit, a communication interface, or the like. The storage module 1121 may be a memory.

Figure 6:
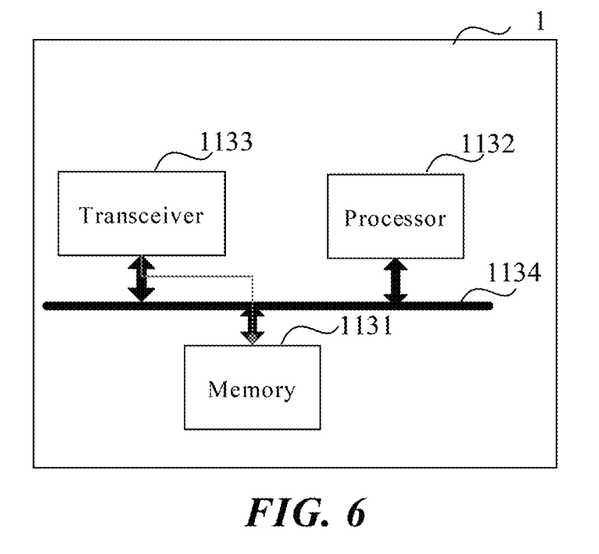
FIG. 6 is a structural schematic diagram of yet another intelligent blind guide apparatus provided by an embodiment of the present disclosure.

In the case that the processing module 1122 is a processor, the communication module 1123 is a transceiver, and the storage module 1121 is a memory, the intelligent blind guide apparatus involved in the embodiment of the present disclosure may be the server as shown in FIG. 6.

As shown in FIG. 6, the server 1 includes a processor 1132, a transceiver 1133, a memory 1131 and a bus 1134. The transceiver 1133, the processor 1132 and the memory 1131 are connected to each other through the bus 1134; the bus 1134 may be a peripheral component interconnect (PCI) bus, an extended industry standard architecture (EISA) bus, or the like. The bus may be divided into an address bus, a data bus, a control bus, and the like. For ease of representation, the bus is only expressed by a thick line in FIG. 6, but it does not mean that there is only one bus or one type of bus.

The steps of the method or algorithm described in combination with the contents disclosed by the present disclosure may be implemented in the form of hardware and may also be implemented by a processor executing software instructions. The embodiment of the present disclosure further provides a storage medium. The storage medium may include a memory 1131, configured to store a computer software instruction used by the intelligent blind guide apparatus, and the computer software instruction includes a program code designed to execute a human-computer hybrid decision method. Specifically, the software instruction may be composed of corresponding software modules, and the software modules may be stored in a random access memory (RAM), a flash memory, a read only memory (ROM), an erasable programmable read-only memory (EPROM), an electrically EPROM (EEPROM), or any other form of storage medium known in the art. An exemplary storage medium is coupled to the processor, so that the processor may read information from and write information to the storage medium. The storage medium may also be a constituent part of the processor. The processor and the storage medium may be located in an ASIC. Additionally, the ASIC may be located in the intelligent blind guide apparatus. The processor and the storage medium may also exist as discrete components in the intelligent blind guide apparatus.

The embodiment of the present disclosure further provides a computer program. The computer program may be directly loaded into the memory 1131 and contains a software code, and the computer program may implement the above human-computer hybrid decision method after being loaded and executed by a computer.

The foregoing descriptions are merely specific embodiments of the present disclosure, but the protection scope of the present disclosure is not limited thereto. Anyone of skill in the art could readily think of variations or substitutions within the disclosed technical scope of the present disclosure, and these variations or substitutions shall fall within the protection scope of the present disclosure. Accordingly, the protection scope of the present disclosure should be subject to the protection scope of the claims.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An intelligent blind guide method, comprising:
   obtaining, through a sensor, sensed information about an environment surrounding an intelligent blind guide;
   obtaining a confidence value of the intelligent blind guide by evaluating the sensed information, wherein the confidence value of the intelligent blind guide indicates the reliability of blind guide information generated by processing the sensed information; and
   generating blind guide information by processing the sensed information using an artificial intelligence algorithm in a case that the confidence value of the intelligent blind guide is greater than or equal to a threshold, and triggering artificial blind guide in a case that the confidence value of the intelligent blind guide is less than the threshold;
   wherein the obtaining the sensed information includes obtaining sensed information on at least two different categories of information about the environment;
   wherein the obtaining the confidence value of the intelligence blind guide includes analyzing the sensed information on the at least two different categories of information about the environment; and
   wherein the analyzing the sensed information on the at least two different categories of information about the environment includes:
      obtaining confidence sub-values on one or more of: positioning accuracy confidence, obstacle avoidance success confidence and object identification confidence; and
      fusing at least two of the obtained confidence sub-values to obtain the confidence value of the intelligent blind guide.

2. The method according to claim 1, wherein the sensed information comprises ultrasonic sensed information and visual sensed information.

3. The method according to claim 1, wherein the generating the blind guide information by processing the sensed information using the artificial intelligence algorithm includes:
   generating one or more of the following information according to the sensed information:
   current position coordinates, current travelable direction and object identification tag.

4. The method of claim 1, wherein the at least two different categories of information include positioning information, obstacle information or object identification information.

5. The method according to claim 1, wherein the obtaining the positioning accuracy confidence includes obtaining the positioning accuracy confidence according to one or more of the following parameters: texture quality, number of tracking or quality of motion.

6. The method according to claim 1, wherein the obtaining the obstacle avoidance success confidence includes:
   analyzing a size ratio of a passable area in a scene view based on a depth reconstruction result; and
   determining the obstacle avoidance success confidence according to the obtained size ratio.

7. The method according to claim 1, wherein the obtaining the object identification confidence includes:
   extracting features in an image;
   matching the extracted features with a pre-trained feature library; and
   determining the object identification confidence according to a result of the matching.

8. A non-transitory computer storage medium, storing computer executable instructions used with an intelligent blind guide apparatus, the computer executable instructions, when executed by a processor, configures the processor to implement actions comprising:
   causing a sensor to obtain sensor information about an environment surrounding an intelligent blind guide;
   obtaining a confidence value of the intelligent blind guide by evaluating the sensor information; and
   generating blind guide information by processing the sensor information using an artificial intelligence algorithm in a case that the confidence value of the intelligent blind guide is greater than or equal to a threshold, and triggering artificial blind guide in a case that the confidence value of the intelligent blind guide is less than the threshold;
   wherein the obtaining the sensor information includes obtaining sensor information on at least two different categories of information about the environment;
   wherein the obtaining the confidence value of the intelligence blind guide includes analyzing the sensor information on the at least two different categories of information about the environment; and
   wherein the analyzing the sensor information on the at least two different categories of information about the environment includes:
      obtaining confidence sub-values on one or more of: positioning accuracy confidence, obstacle avoidance success confidence and object identification confidence; and
      fusing at least two of the obtained confidence sub-values to obtain the confidence value of the intelligent blind guide.

9. The computer storage medium according to claim 8, wherein the sensor information comprises ultrasonic sensor information and visual sensor information.

10. The computer storage medium according to claim 8, wherein the generating the blind guide information by processing the sensor information using the artificial intelligence algorithm includes:
   generating one or more of the following information according to the sensor information: current position coordinates, current travelable direction and object identification tag.

11. The computer storage medium according to claim 8, wherein the obtaining the confidence sub-value on the positioning accuracy confidence includes obtaining the positioning accuracy confidence according to one or more of the following parameters: texture quality, number of tracking or quality of motion.

12. The computer storage medium according to claim 8, wherein the obtaining the confidence sub-value on the obstacle avoidance success confidence includes:
   analyzing a size ratio of a passable area in a scene view based on a depth reconstruction result; and
   determining the obstacle avoidance success confidence according to the obtained size ratio.

13. The computer storage medium according to claim 8, wherein the obtaining the confidence sub-value on the object identification confidence includes:
   extracting features in an image;
   matching the extracted features with a pre-trained feature library; and
   determining the object identification confidence according to a result of the matching.

14. A system, comprising:
   a processor;
   a communication interface configured to perform data transmission between the server and an external device; and
   a memory storing computer executable instructions, which when executed by the processor, configures the processor to conduct actions including:
   causing a sensor of the external device to obtain sensor information about an environment surrounding the external device;
   receiving data on the sensor information from the external device;
   evaluating the sensor information to obtain an evaluation value; and
   generating a feedback information about the environment by processing the sensor information using an artificial intelligence algorithm in a case that the evaluation value is greater than or equal to a threshold, and triggering human intervention in a case that the evaluation value is less than the threshold;
   wherein the obtaining the sensor information includes obtaining sensor information on at least two different categories of information about the environment;
   wherein the evaluating the sensor information includes analyzing the sensor information on the at least two different categories of information about the environment; and
   wherein the analyzing the sensor information on the at least two different categories of information about the environment includes:
      obtaining confidence sub-values on one or more of: positioning accuracy confidence, obstacle avoidance success confidence and object identification confidence; and
      fusing at least two of the obtained confidence sub-values to obtain the confidence value of the intelligent blind guide.

15. The system of claim 14, wherein the at least two different categories of information include positioning information, obstacle information or object identification information.

16. The system according to claim 14, wherein the obtaining the confidence sub-value on the positioning accuracy confidence includes obtaining the positioning accuracy confidence according to one or more of the following parameters: texture quality, number of tracking or quality of motion.

17. The system according to claim 14, wherein the obtaining the confidence sub-value on the obstacle avoidance success confidence includes:
   analyzing a size ratio of a passable area in a scene view based on a depth reconstruction result; and
   determining the obstacle avoidance success confidence according to the obtained size ratio.

18. The system according to claim 14, wherein the obtaining the confidence sub-value on the object identification confidence includes:
  extracting features in an image;
  matching the extracted features with a pre-trained feature library; and
  determining the object identification confidence according to a result of the matching.

\* \* \* \* \*